United States Patent [19]
Tsuchiya et al.

[11] Patent Number: 6,080,391
[45] Date of Patent: Jun. 27, 2000

[54] REDUCTION OF MALODOUR

[75] Inventors: Rie Tsuchiya, Birkerød; Bent Riber Petersen, København, both of Denmark

[73] Assignee: Novo Nordisk A/S, Bagvaerg, Denmark

[21] Appl. No.: 09/135,063

[22] Filed: Aug. 13, 1998

[30] Foreign Application Priority Data

Aug. 14, 1997 [DK] Denmark .................. 0936/97

[51] Int. Cl.⁷ .................. A61K 7/32; A61K 7/16; A61K 7/28; A61L 9/00; A61L 11/00
[52] U.S. Cl. .................. 424/65; 424/49; 424/50; 424/76.1; 424/76.5; 424/76.6; 424/94.4; 424/401
[58] Field of Search .................. 424/401, 49, 50, 424/65, 76.1, 76.5, 76.6, 94.4

[56] References Cited

U.S. PATENT DOCUMENTS 4,026,814  5/1977  Johnson et al. .................. 510/392
5,804,170  9/1998  Negishi et al. .................. 424/65

FOREIGN PATENT DOCUMENTS

WO 95/27046  10/1995  WIPO .
96/10079  4/1996  WIPO .
WO 96/10079  4/1996  WIPO .

OTHER PUBLICATIONS

Abstract JP09038183 A, Feb. 10, 1997 Heisei.

*Primary Examiner*—Shelley A. Dodson
*Assistant Examiner*—Marina Lamm
*Attorney, Agent, or Firm*—Steve T. Zelson; Valeta Gregg

[57] ABSTRACT

The present invention relates to the use of one or more oxidoreductases in combination with a mediator for the reduction of malodour. Malodour reducing compositions and products comprising such composition are also claimed.

19 Claims, 2 Drawing Sheets

REDUCTION OF MALODOUR

FIELD OF THE INVENTION

The present invention relates to the use of an oxidoreductase for removing malodour, a malodour reducing composition, and products comprising a composition of the invention.

BACKGROUND OF THE INVENTION

It is well established that malodour may be caused by a number of compounds, such as volatile sulphur compounds (VSC), nitrogen containing compounds, short fatty acids etc.
Volatile Sulphur Compounds (VSC)
Bad Breath Malodour in the form of a bad breath emanating from the oral cavity is typically a consequence of volatile sulphur compounds (VSC). VSCs are produced by oral anaerobic Gram-positive bacteria by degradation of sulphur containing proteinaceous substrates in the salvia. The VSCs are released into the oral environment where they are mixed with air expired from the lungs resulting in a unpleasant odour coming out of the mouth. The above mentioned proteinaceous substrates may be owing to the intake of foods, such as meat, fish, spices, vegetables, dairy products etc. Volatile Sulphur Compounds such as for instance diallyl sulfide, (a thioether) can be found in e.g. garlic being well known for causing a repellent bad breath.
Burned flavour When heat treating certain foods, such as UHT-treating milk, a "burned" flavour caused by Volatile Sulphide Compounds may arise.

Examples of VSCs are hydrogen sulfide ($H_2S$), dimethyl sulfide ($CH_3SCH_3$), diallyl sulfide, and the one being regarded as the most potent methyl mercaptan ($CH_3SH$) also called methanethiol.
Nitrogen containing compounds Nitrogen containing compound such as ammonia, indole, skatole and a number of amines are also well-known to give a bad smell.

An amine such as trimethylamine gives a fishy smell.
Diapers and the like:

A source of nitrogen containing compounds are urine, faeces and blood giving a bad smell known by most people from either soiled diapers or other hygiene products, such as adult incontinence products, training pants, feminine napkins, tampons and the like.

The bad smell coming from diapers and the like is typically a consequence of growth of bacteria, especially *Escherichia coli, Enterococcus faecalis* and *Proteus mirabilis,* present on the skin in the perineum (the region between the anus and the external sexual organs). All strains of Proteus form the enzyme urease during their metabolism. Urease has the ability to rapidly break down urea (constituting about 2% of human urine) into ammonia causing an unpleasant odour.
Short fatty acids Short fatty acids, such as butyric acid (C4), are also know to give a malodour. After having worn shoes for a whole long warm day most people know the bad smell of perspiring feet caused by the short fatty acids such as butyric acid.

Further, clothes washed with a laundry detergent comprising a lipase sometimes have an unattractive odour resembling the odour of spit-up from babies. This malodour is believed to arise when the lipase degradation product of triglyceride containing soils on the fabric is not completely removed during the wash or rinse cycle. Said degradation product consists of short free fatty acids (e.g. butyric acid).

Removal or reduction of malodour

A number of odour controlling agent and systems have been described in the literature. For instance, carbon is e.g. in the form of activated carbon well-known for its ability to adsorb odoriferous molecules.

U.S. Pat. No. 5,593,398 discloses protective underwear with malodorous flatus filter comprising activated carbon as the malodour controlling agent.

Zeolitic materials have been shown to be effective against malodour associated with body fluids.

JP patent application no. 02068117 relates to deodorising means e.g. for diapers containing zeolite, copper and activated charcoal.

U.S. Pat. No. 4,026,814 concerns a soap with a reduced tendency to generate malodours during storage. The soap comprises an enzyme system which contains an oxidoreductase enzyme such as alcohol dehydrogenase and/or aldehyde dehydrogenase, and a hydrogen acceptor selected from the group of nicotinamide-adenine-dinucleotide and/or nicotinamide-adenine-dinucleotide phosphate.

JP patent application no. 9038183 (Takasago Perfumery Co Ltd.) concerns a deodorant composition capable of removing the smell of bad breath, refrigerator, pets etc. The composition comprise of phenolic compounds and an enzyme which oxidise phenolic compounds. As preferred phenolic compounds the following diphenolic compounds are mentioned: cathecol, catechin compounds, tyrosine and chlorogenic acid. Tyrosinase, peroxidase, glucose oxidase, and laccase are mentioned as the oxidative enzyme. Preferred enzymes are of mushroom belonging to *Agrinus bisporus* var. *albidus* and *Boletus pulverulentus.* or of fruit origin, such as apple, pear (gobou).

U.S. Pat. No. 3,903,259 concerns a method of deodorising diapers and human excreta comprising applying to the diapers or the excreta a chemical composition which in its simplest form consists of an acidic material, an antibiotic material, and a solvent. The impregnating composition may also contain a chelating agent and a wetting agent. The treatment of diapers results in a marked decrease in offensive odours from excreta, thus making the changing of sorted diapers less unpleasant.

U.S. Pat. No. 3,935,862 discloses a disposable diaper comprising means for inhibiting ammonia formation therein including an aminopolycarboxylic acid compound in an amount of at least 0.001 gm. per square inch.

U.S. Pat. No. 4,385,632 concerns a germicidal absorbent body for collecting blood, faeces and urine which contains a water-soluble copper salt which impedes bacterial growth, prevents the breaking down of urea into ammonia and complex-binds ammonia so as to prevent the occurrence of unpleasant odour.

U.S. Pat. No. 4,551,187 describes a deodorant body cleansing composition in the form of a liquid or solid opaque bar, comprising a detergent and a specific carbohydrate capable of reducing the odour-causing bacterial population on the body (skin and/or hair), without the use of antimicrobials. The essential deodorant agent which is a group of carbohydrates specifically effective against the odour-causing bacteria on the skin and/or hair, are mannose, glucose, and oligomers thereof, i.e. dimers, trimers, and tetramers.

U.S. Pat. No. 5,395,555 concerns an aqueous cleaning composition for carpets, rugs, and textiles particularly useful in reducing malodour of urine stains. The composition comprising a) from about 4.23% to about 4.28% by weight of a sodium or potassium salt of a diethylenetriaminepentaacetic acid, an ethylenediaminetetraacetic acid, a N-hydroxyethylethylenediaminetriacetic acid, or mixtures thereof; b) from about 1.95% to about 2.05% by weight of a diethylenetriaminepentaacetic acid, an ethylenediaminetetraacetic acid, a N-hydroxyethylethylenediaminetriacetic acid, or a mixture thereof; C) from about 0.82k to 0.98% of a sodium lauryl sulfate; d) from about 0.49% to 0.59% by weight of an acrylate copolymer of the formula $CF_3$ $(CF_2)$ $nCH_2OCOC(CH_3)=CH_2$ wherein n is from 6 to 8; e) from about 0.22% to about 0.27% by weight of an octylphenoxypolyethoxy ethanol; f) from about 0.35% to about 0.5% by weight of fragrance; and g) from about 0.00003% to about 0.05% by weight of a preservative 1,2-benzoisothiazole-3 (2H)-ones.

SUMMARY OF THE INVENTION

It is the object of the present invention to provide improved compositions capable of reducing malodour and products comprising such compositions.

In the first aspect the invention relates to the use of one or more oxidoreductases in combination with a mediator for the reduction of malodour.

It is also an object of the invention to provide malodour reducing compositions comprising one or more oxidoreductases and a mediator, such as oral care and detergent compositions.

Furthermore the invention relates to a product comprising a composition of the invention. Contemplated products include oral care products, such as dentifrice, hygiene products, such as a diaper and the like having a malodour reducing composition incorporated in the body fluid material, food products, such as UHT-milk, toiletries product and personal care products and detergents such as solid and liquid washing detergents.

DETAILED DESCRIPTION OF THE INVENTION

It is the object of the present invention to provide improved compositions capable of reducing malodour and products comprising such malodour reducing compositions.

In the context of the present invention the term "malodour" means an unpleasant bad smell and/or taste/flavour caused by one of the following types of compounds: VSCs, nitrogen containing compounds and short fatty acids, or a combination thereof.

The inventors have found that the removal or at least reduction of malodour can be obtained by the use of one or more oxidoreductases in combination with a mediator.

The term "reducing the malodour" or "reduced malodour" means that the malodour determined by a test panel is assessed to be less pronounced in comparison to a corresponding blind sample not having been exposed to one or more oxidoreductases and a mediator.

Without being limited to any theory it is believed that the mediator sort of link to the volatile sulphur and nitrogen containing compounds resulting in a reaction product which do not have the bad smell. Another theory is that the mediator mediate the linking together of two or more volatile compounds into a compound without or with reduced bad smell.

Oxidoreductases

Oxidoreductases (i.e. enzymes classified under the Enzyme Classification number E.C. 1 (Oxidoreductases) in accordance with the Recommendations (1992) of the International Union of Biochemistry and Molecular Biology (IUBMB)) which are enzymes catalysing oxidoreductions. According to the invention three types of oxidoreductases are especially contemplated:

a) Laccases or related enzymes such as tyrosinase cover enzymes which act on molecular oxygen ($O_2$) and yield water ($H_2O$) without any need for peroxide (e.g. $H_2O_2$),
b) Oxidases cover enzymes which act on molecular oxygen ($O_2$) and yield peroxide ($H_2O_2$), and
c) Peroxidases cover enzymes which act on peroxide (e.g. $H_2O_2$) and yield water ($H_2O$).

Preferred oxidoreductases are of microbial origin, especially recombinant and/or substantially purified enzymes without any side activity. Microbial enzymes are superior to plant and fruit enzymes as they can be produced more easily in large amounts by recombinant techniques known in the art.

Microbial enzyme means in the context of the present invention enzymes derived from bacteria, filamentous fungi or yeasts.

In the case of an enzyme acting on oxygen ($O_2$) as the acceptor, said oxygen may be molecular oxygen supplied by the air.

Also enzyme systems which comprise a combination of the three types of enzymes are contemplated according to the invention. enzyme systems may e.g. consist of a laccase or a related enzyme and an oxidase; a laccase or a related enzyme and a peroxidase; a laccase or a related enzyme and an oxidase and a peroxidase; or an oxidase and a peroxidase.

Laccase and related enzymes

Examples of specifically contemplated enzymes within the group of laccases and related enzymes which are capable of oxidising VSCs and nitrogen compounds in question are mono- and diphenolic oxidases, such as catechol oxidase (1.10.3.1), laccase (E.C. 1.10.3.2), tyrosinase (E.C. 1.14.18.1)(E.C. 1.10.3.1), and bilirubin oxidase (E.C. 1.3.3.5).

Laccase oxidizes o-diphenol as well as p-diphenol forming their corresponding quinones. Tyrosinase or catechol oxidase catalyses two different reactions: The hydroxylation of monophenols in o-diphenols and the oxidation of o-diphenols in o-quinones.

Laccases employed may be derived from a strain of Polyporus sp., in particular a strain of *Polyporus pinsitus* (also called *Trametes villosa*) or *Polyporus versicolor*, or a strain of Myceliophthora sp., e.g. *M. thermophila* or a strain of Rhizoctonia sp., in particular a strain of *Rhizoctonia praticola* or *Rhizoctonia solani,* or a strain of Scytalidium sp., in particular *S. thermophilium,* or a strain of Pyricularia sp., in particular *Pyricularia oryzae,* or a strain of Coprinus sp., such as a *C. cinereus.*

The laccase may also be derived from a fungus such as Collybia, Fomes, Lentinus, Pleurotus, Aspergillus, Neurospora, Podospora, Phlebia, e.g. *P. radiata* (WO 92/01046), Coriolus sp., e.g. *C. hirsitus* (JP 2-238885), and Botrytis, In a preferred embodiment of the invention the laccase is derived from a strain of Myceliophthora sp., especially the *Myceliophthora thermophila* laccase described in WO 95/33836 (from Novo Nordisk).

Bilirubin oxidase may be derived from a strain of Myrothecium sp., such as a strain of *M. verrucaria*.

Peroxidases

Peroxidases must be used in combination with either $H_2O_2$ or an oxidase to obtain the desired result, i.e. removal or at least reduction of malodour.

Suitable peroxidases can be found within the group of enzymes acting on peroxide as acceptor, e.g. E.C. 1.11.1, especially peroxidase (E.C. 1.11.1.7).

Specific examples of suitable enzymes acting on peroxide as acceptor include peroxidases derived from a strain of the fungus species Coprinus, in particular a strain of *Coprinus cinereus* or *Coprinus macrorhizus*, or derived from a strain of the bacteria genus Bacillus, in particular a strain of *Bacillus pumilus*.

Haloperoxidases are also suitable according to the invention. Haloperoxidases form a class of enzymes which are able to oxidise halides (Cl—, Br—, I—) in the presence of hydrogen peroxide to the corresponding hypohalous acids. A suitable haloperoxidase is derivable from Curvularia sp., in particular *C. verruculosa*.

Oxidases

Oxidases yielding peroxide ($H_2O_2$) must be used in combination with a peroxidase to be able to remove or at least reduce malodour.

Suitable oxidases include glucose oxidase (E.C. 1.1.3.4), hexose oxidase (E.C. 1.1.3.5), L-amino-acid oxidase (E.C. 1.4.3.2), xylitol oxidase, galactose oxidase (E.C. 1.1.3.9), pyranose oxidase (E.C. 1.1.3.10), alcohol oxidase (E.C. 1.1.3.13).

If a L-amino acid oxidase is used it may be derived from a Trichoderma sp. such as *Trichoderma harzianum*, such as the L-amino acid oxidase described in WO 94/25574 (from Novo Nordisk A/S), or *Trichoderma viride*.

A suitable glucose oxidase may originate from Aspergillus sp., such as a strain of *Aspergillus niger*, or from a strain of Cladosporium sp. in particular *Cladosporium oxysporum*.

Hexose oxidases from the red sea-weed *Chondrus crispus* (commonly known as Irish moss) (Sullivan and Ikawa, (1973), Biochim. Biophys. Acts, 309, p. 11–22; Ikawa, (1982), Meth. in Enzymol. 89, carbohydrate metabolism part D, 145–149) oxidises a broad spectrum of carbohydrates, such as D-glucose, D-galactose, is maltose, cellobiose, lactose, D-glucose 6-phasphate, D-mannose, 2-deoxy-D-glucole, 2-deoxy-D-galactose, D-fucase, D-glucurnic acid, and D-xylose.

Also the red sea-weed *Iridophycus flaccidum* produces easily extractable hexose oxidases, which oxidise several different mono- and disaccharides (Bean and Hassid, (1956), J. Biol. Chem, 218, p. 425; Rand et al. (1972, J. of Food Science 37, p. 698–710).

Another suitable group of enzyme is xylitol oxidase (see e.g. JP 80892242) which oxidises xylitol, D-sorbitol, D-galactitol, D-mannitol and D-arabinitol in the presence of oxygen. A xylitol oxidase can be obtained from strains of Streptomyces sp. (e.g. Streptomyces IKD472, FERM P-14339). Said enzyme has a pH optimum at 7.5 and is stable at pH 5.5 to 10.5 and at temperatures up to 65° C. 30 In the case of reducing malodour emanating from the oral cavity e.g. by incorporation of an oxidoreductase in an oral care product it is advantageous to use enzymes being substantially active at pHs prevailing in the mouth, i.e. between pH 5.0 to 9.0, preferably between pH 6.0 to 8.5, especially between pH 6.4 to 7.5 and at temperature in the range from 25° C. to 40° C.

The term "substantially active" enzyme means in this context that the enzyme(s) has(have) an relative activity (pH-optimum defines 100% at the same conditions) higher than 30%, better 50%, even better more than 70%, such as 80%, and in the best case up to about 100% of the activity at the pH optimum.

Mediator

According to the invention the one or more oxidoreductases are used in combination with a suitable redox mediator. A so-called "redox mediator" is sometimes in literature referred to as "an enhancing agent". In the present context the term "mediator" will be used.

A "mediator" is an agent capable of enhancing the activity of oxidoreductases.

The mediator may be a phenolic mediator or a non-phenolic mediator. Which mediator is preferred depends of the purpose. If the concept of the invention is to be used for oral care application or a food application the mediator should preferably be non-toxic.

Examples mediators capable of enhancing the activity of oxidoreductases include the compounds described in WO 95/01426, which is hereby incorporated by reference, and described by the general formula I:

The definition of the R1 to R10 and A groups can be found in WO 95/010426 (see p. 9 to 11).

Specifically contemplated compounds within the above formula I include the following: 2,2'-azino-bis(3-ethylbenzothiazoline-6-sulfonate (ABTS); 6-hydroxy-2-naphtoic acid; 7-methoxy-2-naphtol; 7-amino-2-naphthalene sulfonic acid; 5-amino-2-naphthalene sulfonic acid; 1,5-diaminonaphthalene; 7-hydroxy-1,2-naphthimidazole; 10-methylphenothiazine; 10-phenothiazine-propionic acid (PPT); N-hydroxysuccinimide-10-phenothiazine-propionate; benzidine; 3,3'-dimethylbenzidine; 3,3'-dimethoxy-benzidine; 3,3',5,5'-tetramethylbenzidine; 4'-hydroxy-4-biphenylcarboxylic acid; 4-amino-4'-methoxystilbene; 4,4'-diaminostilbene-2,2'-disulfonic acid; 4,4'-diaminodiphenylamine; 2,7-diaminofluorene; 4,4'-dihydroxy-biphenylene; triphenylamine; 10-ethyl-4-phenothiazinecarboxylic acid; 10-ethylphenothiazine; 10-propylphenothiazine; 10-isopropylphenothiazine; methyl-10-phenothiazinepropionate; 10-phenylphenothiazine; 10-allylphenothiazine; 10-phenoxazinepropionic acid (POP); 10-(3-(4-methyl-1-piperazinyl)propyl)phenothiazine; 10-(2-pyrrolidinoethyl) phenothiazine; 10-methylphenoxazine; iminostilbene; 2-(p-aminophenyl)-6-methylbenzothiazole-7-sulfonic acid; N-benzylidene-4-biphenylamine; 5-amino-2-naphthalenesulfonic acid; 7-methoxy-2-naphtol; 4,4'-dihydroxybenzophenone; N-(4-(dimethylamino) benzylidene)-p-anisidine; 3-methyl-2-benzothiazolinone(4-(dimethylamino)benzylidene)hydrazone; 2-acethyl-10-methylphenothiazine; 10-(2-hydroxyethyl)phenothiazine; 10-(2-hydroxyethyl)phenoxazine; 10-(3-hydroxypropyl) phenothiazine; 4,4'-dimethoxy-N-methyl-diphenylamine, vanillin azine.

Other mediator contemplated include 4-hydroxybenzoic acid, L-tyrosine, syringate acids, ferulic acid, sinapic acid, Chlorogenic acid, caffeic acid and esters thereof.

Still further examples include organic compounds described in WO 96/10079, which is hereby incorporated by reference, and by the following formula II:

in which formula A is a group such as —D, —CH=CH—D, —CH=CH—CH=CH—D, —CH=N—D, —N=N—D, or —N=CH—D, in which D is selected from the group consisting of —CO—E, —SO$_2$—E, —N—XY, and —N'—XYZ, in which E may be —H, —OH, —R, or —OR, and X and Y and Z may be identical or different and selected from —H and —R; R being a $C_1$–$C_{16}$ alkyl, preferably a $C_1$–$C_8$ alkyl, which alkyl may be saturated or unsaturated, branched or unbranched and optionally substituted with a carboxy, sulfo or amino group; and B and C may be the same or different and selected from $C_mH_{2m+1}$; $1 \leq m \leq 5$.

Specific compounds covered by the above formula I are acetosyringone, syringaldehyde, methylsyringate, syringic acid, ethylsyringate, propylsyringate, butylsyringate, hexylsyringate, octylsyringate and ethyl 3-(4-hydroxy-3,5-dimethoxyphenyl)acrylate.

Application of the concept invention

The concept/principle of the invention can be used for a vast number of application.

Burned flavour

The principle of the invention may also be used for removing burned flavour, a problem known in connection with e.g. UHT-treated milk.

Dehairing of hides and skin

During dehairing of hides and skin large amounts of sulfide are usually used. This results in a bad smell caused by VSCs. These VSCs may be reduced according to the invention.

Permanent hair waving

Permanent waving of hair involves breaking and/or restoring disulfide cross linkages giving the shape of the keratineous hair fibers. For this purpose a number of organic reducing agent such as thioglycolic acid, thioactic acid and other sulphur containing compounds are used. The waving process results in a malodour caused by VSCs and amines formed as a side-product. Such malodour can be reduced according to the invention.

Diapers

The malodour removing effect of the combination of one or more oxidoreductases and a mediator can also be used in connection with odour control of body fluids and body gases by incorporation of one or more of the above mentioned oxidoreductases and mediators in hygiene products including diapers, incontinence products, filters for underwear, garment shields etc.

Detergent

It is also contemplated according to the invention to add one or more oxidoreductases and a mediator to a detergent composition, e.g., laundry washing powder, a liquid detergent or the like. The remaining malodour caused by short fatty acids may be reduced this way. The malodour reducing system may also be a part of the softener (i.e. fabric softening composition) added during the washing cycle. Likewise for other detergents such as dish washing detergents.

The detergent compositions may for example, be formulated as hand and machine laundry detergent compositions including laundry additive compositions and compositions suitable for use in the pretreatment of stained fabrics, rinse added fabric softener compositions, and compositions for use in general household hard surface cleaning operations and dishwashing operations.

The detergent composition comprises a lipase, and typically other enzyme activities such as protease activity, as will be described further below, and a surfactant. Additionally, it may optionally comprise a builder, a suds suppresser, a softening agent, a dye-transfer inhibiting agent and other components conventionally used in detergents such as soil-suspending agents, soil-releasing agents, optical brighteners, abrasives, bactericides, tarnish inhibitors, coloring agents, and/or encapsulated or nonencapsula-ted perfumes.

The detergent composition can be in liquid, paste, gels, bars or granular forms. The pH (measured in aqueous solution at use con-centration) will usually be neutral or alkaline, e.g. in the range of 7–11. Granular compositions according to the present invention can also be in "compact form", i.e. they may have a relatively higher density than conventional granular detergents, i.e. form 550 to 950 g/l.

A lipase or optionally another enzyme incorporated in the detergent composition, is normally incorporated in the detergent composition at a level from 0.00001% to 2% of enzyme protein by weight of the composition, preferably at a level from 0.0001% to 1% of enzyme protein by weight of the composition, more preferably at a level from 0.001% to 0.5% of enzyme protein by weight of the composition, even more preferably at a level from 0.01% to 0.2% of enzyme protein by weight of the composition.

The amount of lipase protein may be 0.001–10 mg per gram of detergent or 0.001–100 mg per liter of wash liquor. More specifically, the lipase may be incorporated in the detergent compositions described in WO 97/04079, WO 97/07202, WO 97/41212, and PCT/DK 97/00345.

Surfactant system

The surfactant system may comprise nonionic, anionic, cationic, ampholytic, and/or zwitterionic surfactants. The surfactant system preferably consists of anionic surfactant or a combination of anionic and nonionic surfactant, e.g. 50–100% of anionic surfactant and 0–50% nonionic. The laundry detergent compositions may also contain catio-nic, ampholytic, zwitterionic, and semi-polar surfactants, as well as the nonionic and/or anionic surfactants other than those already described herein.

The surfactant is typically present at a level from 0.1% to 60% by weight. Some examples of surfactants are described below.

Nonionic surfactant

The surfactant may comprise polyalkylene oxide (e.g. is polyethylene oxide) condensates of alkyl phenols. The alkyl group may contain from about 6 to about 14 carbon atoms, in a straight chain or branched-chain. The ethylene oxide may be present in an amount equal to from about 2 to about 25 moles per mole of alkyl phenol.

The surfactant may also comprise condensation products of primary and secondary aliphatic alcohols with about 1 to about 25 moles of ethylene oxide. The alkyl chain of the aliphatic alcohol can either be straight or branched, and generally contains from about 8 to about 22 carbon atoms.

Further, the nonionic surfactant may comprise polyethylene oxide condensates of alkyl phenols, condensa-tion products of primary and secondary aliphatic alcohols with from about 1 to about 25 moles of ethylene oxide, alkylpolysaccharides, and mixtures hereof. Most preferred are C8–C14 alkyl phenol ethoxylates having from 3 to 15 ethoxy groups and C8–C18 alcohol ethoxylates (preferably C10 avg.) having from 2 to 10 ethoxy groups, and mixtures thereof.

Anionic surfactants

Suitable anionic surfactants include alkyl alkoxyla-ted sulfates which are water soluble salts or acids of the formula RO(A)mSO3M wherein R is an unsubstituted C10–C-24 alkyl or hydroxyalkyl group having a C10–C24 alkyl component, preferably a C12–C20 alkyl or hydroxyalkyl, more pre-ferably C12–C18 alkyl or hydroxyalkyl, A is an ethoxy or pro-poxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxy-lated sulfates as well as alkyl propoxylated sulfates are contemplated herein. Specific examples of substituted ammonium ca-tions include methyl-, dimethyl, trimethyl-ammonium cations and quaternary ammo-nium cations such as tetramethyl-ammonium and dimethyl piperdinium cations and those derived from alkylamines such as ethylamine, diethylamine, triethylamine, mixtures thereof, and the like. Other suitable anionic surfactants include the alkyl sulfate surfactants which are water soluble salts or acids of the formula ROSO3M wherein R preferably is a C10–C24 hydrocarbyl, preferably an alkyl or hydroxyalkyl having a C10–C20 alkyl component, more preferably a C12–C18 alkyl or hydroxyalkyl, and M is H or a cation, e.g., an alkali metal cation (e.g. sodium, potassium, lithium), or ammonium or sub-stituted ammonium.

Other anionic surfactants include salts (including, for example, sodium, potassium, ammonium, and substituted am-monium salts such as mono- di- and triethanolamine salts) of soap, C8–C22 primary or secondary alkanesulfonates, C8–C24 olefinsulfonates, sulfonated polycarboxylic acids prepared by sulfonation of the pyrolyzed product of alkaline earth metal citra-tes.

Alkylbenzene sulfonates are suitable, especially linear (straight-chain) alkyl benzene sulfonates (LAS) wherein the alkyl group preferably contains from 10 to 18 carbon atoms.

The laundry detergent compositions typically comprise from about 1% to about 40%, preferably from about 3% to about 20% by weight of such anionic surfactants.

Builder system

The compositions according to the present invention may further comprise a builder system. Any conventional builder system is suitable for use herein including aluminosilicate materials, silicates, polycarboxylates and fatty acids, materials such as ethylenediamine tetraacetate (EDTA), metal ion sequestrants such as aminopolyph-osphonates. Phosphate builders can also be used herein.

Suitable builders can be an inorganic ion exchange material, commonly an inorganic hydrated aluminosilicate material, more particularly a hydrated synthetic zeolite such as hydrated zeolite A, X, B, HS or MAP.

Detergency builder salts are normally included in amounts of from 5% to 80% by weight of the composition. Preferred levels of builder for liquid detergents are from 5% to 30%.

Other enzymes

The detergent composition may besides the lipase comprise other enzyme(s) providing cleaning performance and/ or fabric care benefits, e.g. proteases, lipases, cutinases, amylases, cellulases, peroxidases, oxidases (e.g. laccases).

Suitable proteases include those of animal, vegetable or microbial origin. Microbial origin is preferred. Chemically or genetically modified mutants are included. The protease may be a serine protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279) and variants thereof.

Bleaching agents

The detergent composition (especially in the case of a granular detergent) may also comprise a bleaching agents, e.g. an oxygen bleach or a halogen bleach. The oxygen bleach may be a hydrogen peroxide releasing agent such as a perborate (e.g. PB1 or PB4) or a percarbonate, or it may e.g. be a percarboxylic acid. The particle size may be 400–800 microns. When present, oxygen bleaching compounds will typically be present at levels of from about 1% to about 25%.

The hydrogen peroxide releasing agent can be used in combination with bleach activators such as tetraacetylethylenediamine (TAED), nonanoyloxybenzene-sulfonate (NOBS), 3,5-trimethyl-hexsanoloxybenzene-sulfonate (ISONOBS) or pentaacetylglucose (PAG).

The halogen bleach may be, e.g. a hypohalite bleaching agent, for example, trichloro isocyanuric acid and the sodium and potassium dichloroisocyanurates and N-chloro and N-bromo alkane sulphonamides. Such materials are normally added at 0.5–10% by weight of the finished product, preferably 1–5% by weight.

Food malodour

Foodstuffs such as fish, meat and the like give a malodour primarily caused by nitrogen containing compounds. The amine trimethylamine which is known to give a fishy smell can be reduced according to the invention.

Waste water/and gas

The concept of the invention can also be used for removal of amines and VSCs in waste water and exhaust gasses.

Toiletries

The use of the malodour reducing system of the invention as an active ingredient in toiletries, bath and shower products, including shampoos, conditioners, lotions, creams, soap bars, toilet soaps, and liquid soaps and other personal care products are also contemplated. The development of body malodour is believed largely to be due to bacterial action on the products of sweat glands.

Cleaning compositions

Another application where the principle of the invention can be used is in cleaning composition for carpets, rugs, garment, textiles and the like.

The practical incorporation of the concept of the invention as defined in the claims can easily be carried out by a skilled person. A person skilled in the art can easily adapt the concept of the invention to specific types products where malodour control or removal or reduction of malodour are known to be desired.

Composition

In a second aspect the invention relates to a malodour removing or reducing composition comprising one or more oxidoreductases and a mediator.

The oxidoreductases and the mediator may be the ones disclosed above in connection with the first aspect of the invention.

Oral care

A composition of the invention may be used in oral care products.

An oral care product according to the invention capable of removing malodour emanating from the oral cavity may have any suitable physical form (i.e. powder, paste, gel, liquid, ointment, tablet etc.).

An "oral care product" can be defined as a product which can be used for maintaining or improving the oral hygiene in the mouth of humans and animals, by e.g. preventing dental caries, preventing the formation of dental plaque and tartar, removing dental plaque and tartar, preventing and/or treating dental diseases, removing malodour etc.

Oral care products do also encompass products for cleaning dentures, artificial teeth and the like.

Examples of oral care products include toothpaste, dental cream, gel or tooth powder, odontic, mouth washes, pre- or post brushing rinse formulations, chewing gum, lozenges, and candy.

Toothpastes and tooth gels typically include abrasive polishing materials, foaming agents, flavouring agents, humectants, binders, thickeners, sweetening agents, whitening/bleaching/stain removing agents, water, and optionally enzymes.

Mouth washes, including plaque removing liquids, typically comprise a water/alcohol solution, flavour, humectant, sweetener, foaming agent, colorant, and optionally enzymes.

Product

In the third aspect the invention relates to products comprising a malodour removing or reducing composition of the invention.

The composition of the invention may be used in oral care products such as dentifrice, toiletries, detergents, fabric softeners, foods.

Other examples of contemplated products include hygiene products, such as diapers, adult incontinence products, training pants, feminine napkins, tampons; toiletry products, such as soap bars and the like; products for removing burned flavour from foods, such as milk etc.

According to the invention the product may be a one or a two compartment product. In the one compartment product the oxidoreductase, the mediator and other ingredients are keep together in a stabilised solution or kept under stable conditions (i.e. so that no oxygen is present). In a two compartment product the oxidoreductase and the mediator and other ingredients are keep in two containers keep apart. The contents of said containers are mixed before use.

METHODS AND MATERIALS

Materials:

Enzyme:

Laccases

Recombinant laccase from *Myceliopthora thermophila* (rMtL)(available from Novo Nordisk) and described in WO 95/33836 (Novo Nordisk).

Recombinant Coprinus cinereus laccase (rCcL).

Recombinant Polyporus pinsitus laccase (rPpL).

Tyrosinase

Tyrosinase T-7755 from Mushroom/Sigma.

Peroxidase

Recombinant Coprinus cinereus peroxidase (rCiP)

Horse radish peroxidase Type I/Sigma P-8125

Horse radish peroxidase Type XII/Sigma P-8415

Acid horse radish peroxidase: RZ 2.5, pI 4, 5.3, 5.85 and 6.0. Does not bind to benzhydroxonic acid agarose.

Reagents:

Mediator: 10-phenothiazine-propionic acid (PPT); 10-phenoxazinepropionic acid (POP); caffeic acid; Chlorogenic acid; L-Tyrosine; p-hydroxybenzoic acid; Syringaldehyde; Methylsyringate. Sodium methanethiolate (purchased from Fluka) Buffer: Britten-Robinson buffer at pH indicated in the examples.

GC Chromatograph:

Column: 6 ft×⅛ in. o.d. teflon column packed with 40/60 mesh carbopack BHT-100 (Supelco).

Detector: Flame Photometric Detector (FPD) (Hewlett Packard) Air flow: 100 ml/min (350 kPa)

$H_2$: 75 ml/min (150 kPa)

Carrier+make-up: 30 ml/min (130 kPa)

Chromatographic conditions:

| 30 ml/minute of $N_2$ and He | |
|---|---|
| Injector temperature | 150° C. |
| Detector temp. | 200° C. |
| Initial oven temp. | 35° C. |
| Initial time | 2.5 minute |
| Rate | 10° C./minute |
| Final temp | 140° C. |

Methods

Determination of Laccase Activity (LAMU)

The LAMU method is used for determining the activity of *Myceliophthora thermophila* laccase.

Laccase (E.C. 1.10.3.2), p-diphenol: $O_2$ oxidoreductase, containing copper in the prosthetic group, uses molecular oxygen as a final electron acceptor. Atmospheric oxygen is directly reduced to 2 $H_2O$, during liberation of 4 electrons, without hydrogenperoxide being an intermediate step.

Laccase will under aerobic conditions catalyse the oxidation of syringaldazine forming tetrametoxy-azo bis methylene quinone.

Tyrosinase activity:

The activity and specific activity of tyrosinase defined according to Duckworth, H. W. and Coleman, J. E. ( 1970) J. Biol. Chem. 245, 1613–1625, was used to calculate the amount of enzyme protein.

Reaction conditions

| Substrate | Syringaldazine 19 mM |
|---|---|
| Buffer | Tris 23 mM |
| pH | 7.50 |
| Temperature | 30° C |
| Time of reaction | 90 seconds. |
| Enzyme working area | 0.0016–0.0064 LAMU/ml |
| Wavelength | 530 nm |
| Water | Milli Q |

Definition of units

One LAMU, is the amount of enzyme which under the given analytical conditions transforms 1 $\mu$mol syringaldazine per minute.

Specificity and Sensitivity

| Limit of detection LOD: | 0.007 LAMU/ml |
|---|---|
| Limit of quantification LOQ: | 0.07 LAMU/ml |
| Range: | 0.100–0.400 ABS/min. |

Reagents/Substrates

Maleic acid, 1.0 M

| | |
|---|---|
| Maleic acid 37% paM*) 800380 | 23.2 g |
| Demineralized water, Milli Q | up to 200 ml |

*)pro analysi Merck 23.2 g Maleic Acid is weighed in a weighing boat and added 150 ml water during continuously stirring. Stir until dissolved.

Transfer quantitatively the solution to a 200 ml volumetric flask and add up to the mark with water.

*)pro analysi Merck

Tris buffer 1.0 M; Stock solution

| | |
|---|---|
| Tris[hydroxymethyl]aminomethane Sigma T-1378 | 121.1 g |
| Demineralized water, Milli Q | up to 1 l |

Tris buffer is weighed in a weighing boat and 800 mL of water go is added during continuously stirring. Stir until dissolved.

Transfer quantitatively the solution to a 1 volumetric flask and add up to the mark with water.

Tris buffer 25 mM; pH 7.50

| | |
|---|---|
| Tris buffer 1.0 M | 25.0 ml |
| Maleic acid, 1.0 M | 5.0 ml |
| Demineralized water | up to 1 l |
| pH is adjusted to 7.50 ± 0.05. | |

Pour 50 ml Tris buffer 1.0 M (graduated glass) into a 1 lvolumetric flask and add about 700 ml water. Now add 5 ml Maleic acid, 1 M. Adjust pH to 7.50±0.05 and add up to the mark with water. (pH may not be adjusted with HCl, because of the inhibiting effect on the Laccase-enzyme.)

Dilution media

| | |
|---|---|
| PEG 6000 paM 807491 | 25.0 g |
| Triton X-100, Sigma T-9284 | 5.0 g |
| Milli Q water up to | 0.5 l |

25.0 g PEG 6000 and 5.0 g Triton X-100 is weighed in a weighing boat and added 400 ml water during continuous stirring. Stir until dissolved.

Transfer quantitatively the solution to a 0.5 l volumetric flask and add up to the mark with water.

Syringaldazine, 0.56 mM; Stock solution

| | |
|---|---|
| Syringaldazine and Sigma S-7896 | 10.0 mg |
| Ethanol 96% | 50 ml |

Syringaldazine is weighed in a 50 ml volumetric flask and added ethanol of 50 ml. Is stirred until dissolved (appr. 3 hours). The reagent is sensitive to light. Should be contained in a dark bottle.

Syringaldazine, 0.28 mM; 48% ethanol

| | |
|---|---|
| Syringaldazine, 0.56 mM | 25.0 ml |
| Demineralized water, Milli Q | up to 50 ml |

25 ml syringaldazine, 0.56 mM (full pipette) is transferred to a 50 ml volumetric flask. Fill up to the mark with water.

Check of the Reagent: Syringaldazine, 0.056 mM; 48% Ethanol:

| | |
|---|---|
| Syringaldazine, 0.2 mM | 2 ml |
| Ethanol, 96% | 4 ml |
| Demineralized water, Milli Q | up to 10 ml |

The solution should have an absorption of about 2.2 at 360 nm. measured against ethanol, 6%.

Ethanol, 6%

| | |
|---|---|
| Ethanol, 96% | 62.5 ml |
| Demineralized water, Milli Q | up to 1000 L |

62.5 ml ethanol, 96% (graduated glass) is transferred to a 1 l volumetric flask. Fill up to the mark with water.

Samples and Standards

Control

The analyses are compared to a well known laccase sample in order to control the level of the assay. The sample is a representative laccase batch.

Unknown samples

The Laccase samples are diluted to an expected activity of 0.18 LAMU/ml with the dilution media. Let the samples rest for 15 minutes before analysis.

Working area: 0.07–0.28 LAMU/ml.

Other samples with precipitate are centrifuged at about 3000 rpm. for 10 minutes.

PROCEDURE

Reagents and standards are made. The samples are weighed and diluted to an expected activity at 0.18 LAMU/ml.

4 ml Tris buffer, 25 mM; pH 7.5 is preheated in at least 10 minutes at 30° C. A 100 ml sample is added. Mixing. 300 ml syringaldazine, 0.28 mM is added whereby the reaction is started. Mixing.

The sample is mounted into the photometer, on which afterwards the kinetic sequence at 530 nm is read, and a change in absorption is calculated per minute from t90 sec.–t60 sec. See table 1 below. Between each sample the photometer cuvette is rinsed with a 6% ethanol solution.

TABLE 1

| Procedure for laccase | |
|---|---|
| Tris buffer 25 mM; pH 7.5 (reagent 6.3) | 4.00 ml |
| Heating, 10 minutes, 30° C. | |
| Enzyme | 100 ml |
| Mixing | |
| Syringaldazine 0.28 mM (reagent 6.6) | 300 ml |
| Mixing | |

TABLE 1-continued

Procedure for laccase

Reading t = 90 sec. at 530 nm
Calculation: t90 sec. −t60 sec.
Rinse with 6% ethanol Calculation $$\Delta ABS \times 0.677 \times D = LAMU/mL$$

$$\frac{\Delta ABS \times 4.4 \times 10^{-3}}{0.065 \times 01} \times D = LAMU/mL$$

Where:
AABS: change in absorption per minute.
4.4: total volume in ml.
0.1: assay volume in ml.
0.065: m molar extinction coefficient.
$10^{-3}$: LAMU/l→LAMU/ml.
D: Further dilution.

EXAMPLES

Example 1

Control Experiment of Sniffing Test

Threshold of sensory test against methanethiol was performed. The known concentration of sodium methanethiolate was prepared in a Britton-Robinson buffer pH 6.5. 2.0 ml of each solution was poured to 20 ml glass bottle. The trained subjects gave score.

As shown in the table below, when score 0 or "no odour" is given to a sample, more than 95% of methanethiol is removed.

| $NaSCH_3$ | 0.11 (reference) | 0.055 | 0.027 | 0.013 | 0.006 | 0.003 |
|---|---|---|---|---|---|---|
| Score | 4 | 4 | 3 | 2 | 1 | 1 |

Score:
4: Reference or odour as reference
3: Clear odour
2: Weak odour
1: Very weak odour
0: No odour

Example 2

Reduction of Malodour (VSC) with Laccase and PTT as Mediator 0.5 µl of 15% sodium methane thiolate ($CH_3SNa$) (0.11 mM) was added to 10.0 ml of 40 mM Britton-Robinson buffer pH 6.0 in a closed 50 ml container.

500 µM PPT and 5 LAMU/ml *Myceliophthora thermophila* laccase were added to the mixture and incubated at 37° C. for 30 minutes. The reaction mixture was shaken manually during incubation.

After the enzyme reaction, 0.1 ml of a gas sample was taken from the head space and GC analysed. A control was made without the laccase and the PPT.

Figure 1:
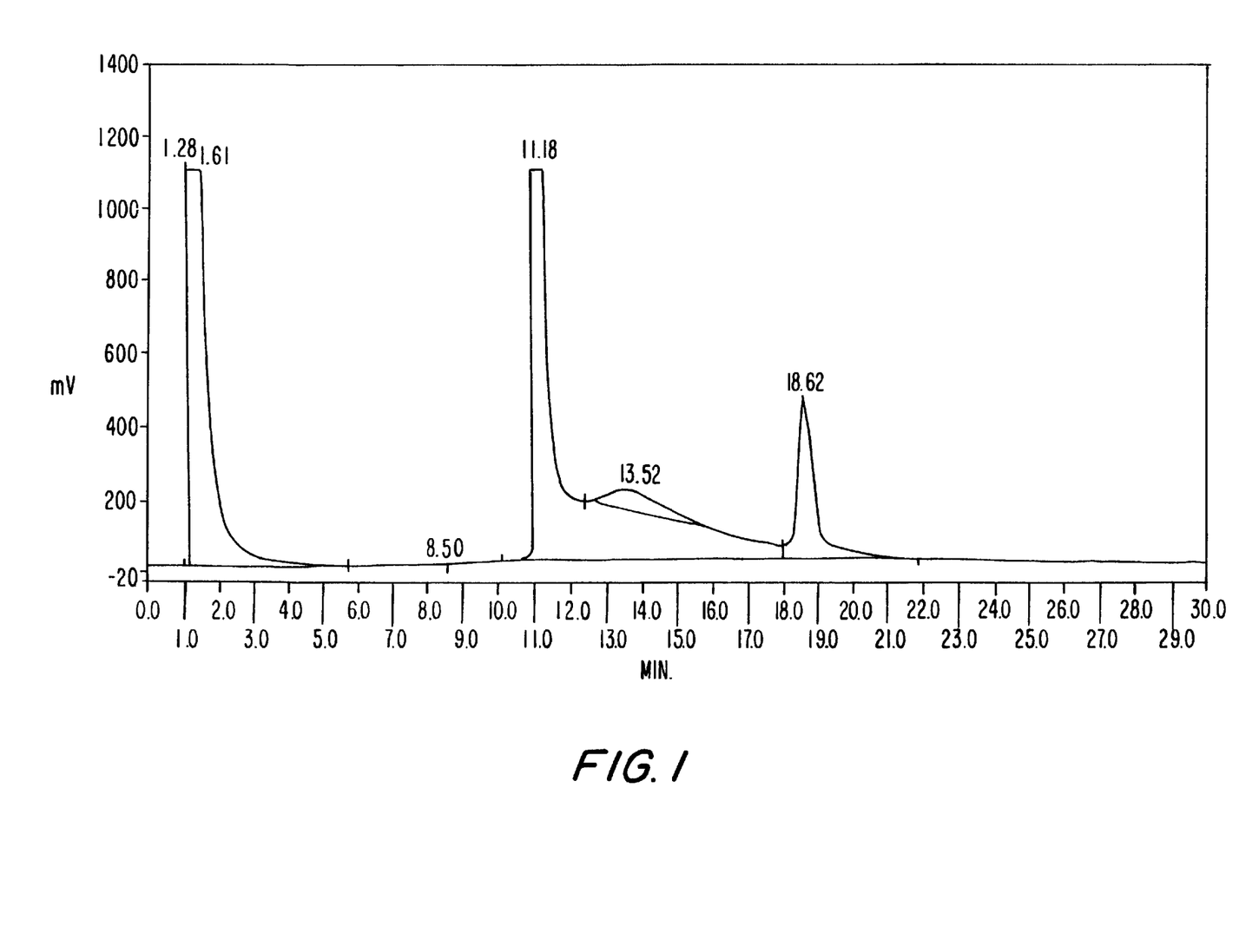
FIG. 1 shows a control GC chromatogram before the enzyme reaction, (no enzyme, no PPT). The peak 1.28–1.61 indicates the presence of methanethiol ($CH_3SH$).

A GC-sniff showed that the first peak at 1 min in a control (FIG. 1) was $CH_3SH$.

Figure 2:
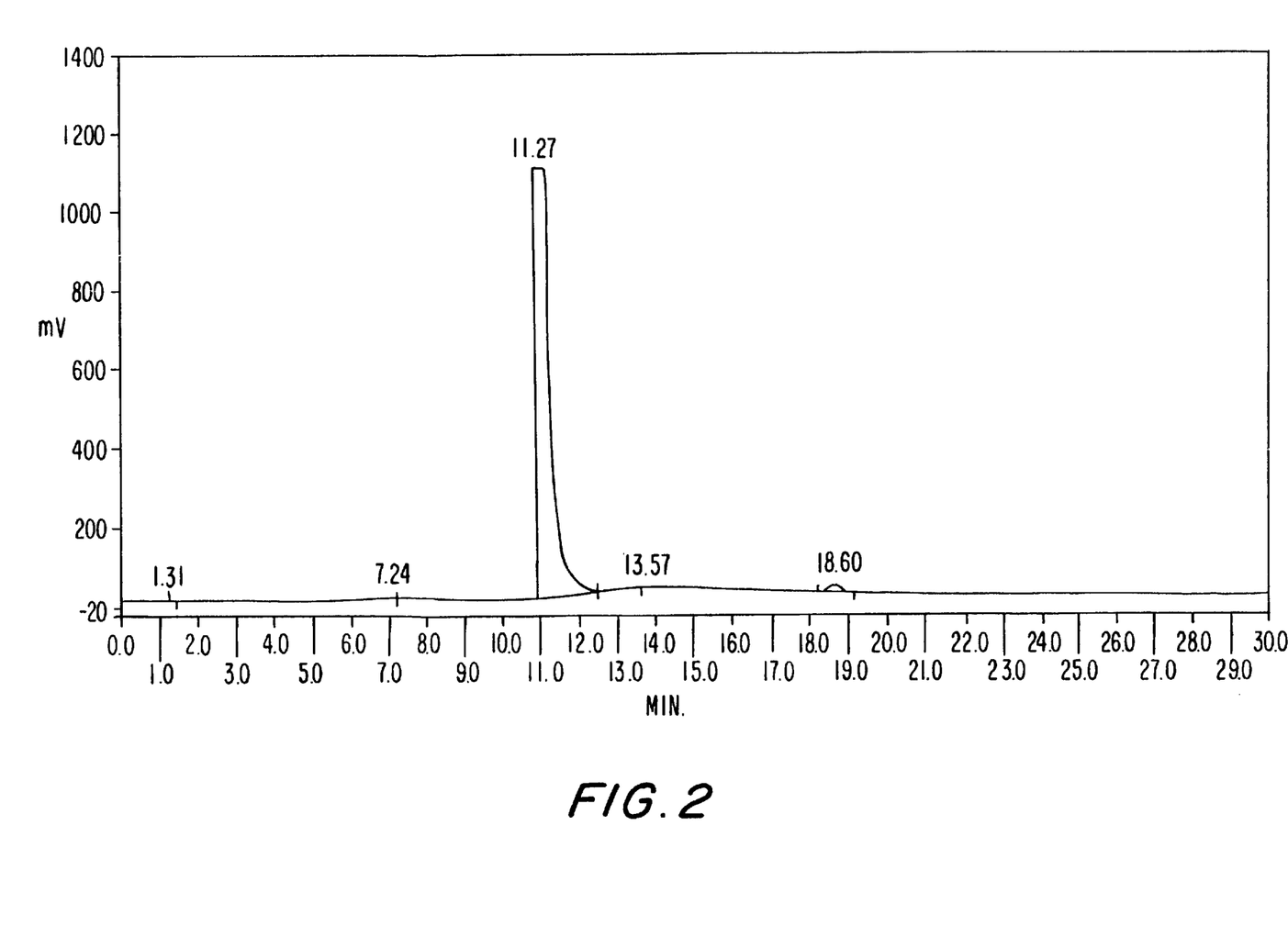
FIG. 2 shows a GC chromatogram obtained after the reaction with enzyme and PPT.

As can be seen from the chromatograms (FIG. 1 and FIG. 2), $CH_3SH$ peak completely disappeared after the enzyme reaction reflecting that the methanethiol malodour had disappeared.

Sniffing Tests

1. Methanethiol ($CH_3SH$) has characteristic odour. After the enzyme reaction the odour was tested by sniffing to the reaction mixture. The malodour had disappeared which indicates that more than 95% of the $CH_3SH$ was removed.

Example 3

Reduction of Malodour (VSC) with Laccase and PPT and POP as Mediators

2 µl of 15% sodium methanethiolate (0.11 mM) was added to 2.0 ml of 40 mM Britton-Robinson buffer in a closed 50 ml container.

The *Myceliophthora thermophila* laccase and either PPT or POP were added according to the table below. The mixture (total volume 2.0 ml) was hand shaken for 10 minutes at room temperature. Malodour was scored.

| Enzyme | Mediator 500 µM | pH | Malodour | |
|---|---|---|---|---|
| 0 | none | 5.5 | +++ | strong methanethiol odour |
| 0 | none | 6.0 | +++ | strong methanethiol odour |
| 5 LAMU/ml | PPT | 5.5 | + | some methanethiol odour |
| 0 | PPT | 5.5 | +++ | strong methanethiol odour |
| 5 LAMU/ml | POP | 5.5 | ± | no methanethiol odour |
| 0 | POP | 5.5 | +++ | strong methanethiol odour |
| 5 LAMU/ml | PPT | 6.0 | ± | no methanethiol odour |
| 0 | PPT | 6.0 | +++ | strong methanethiol odour |
| 5 LAMU/ml | POP | 6.0 | ± | no methanethiol odour |
| 0 | POP | 6.0 | +++ | strong methanethiol odour |

PPT, POP and the laccase gave no odour

As can be seen from the Table laccase in combination with a mediator reduced the VSC malodour significantly.

Example 4

Reduction of in vitro Oral Malodour (VSC)

Tongue plaque was collected from a subject and cultivated in the Brain Heart Infusion (BHI) medium at 37° C. overnight. 0.5 ml culture broth was mixed with 0.5 ml 40 mM Britton-Robinson buffer, pH 6.0, in a 20 ml volume glass container. 500 µM PPT or POP and 5 LAMU/ml *Myceliophthora thermophila* laccase were added to a mixture according to the table below. It was hand shaken for 10 minutes at room temperature. Malodour was scored.

| Enzyme | Mediator 500 µM | pH | Malodour | |
|---|---|---|---|---|
| 0 | none | 6.0 | ++ | strong volatile sulphur odour |
| 5 LAMU/ml | PPT | 6.0 | + | fruity, rather pleasant odour |
| 0 | PPT | 6.0 | ++ | strong volatile sulphur odour |
| 5 LAMU/ml | POP | 6.0 | + | fruity, rather pleasant odour |
| 0 | POP | 6.0 | ++ | strong volatile sulphur odour |

Example 5

Reduction of Malodour (Trimethylamine)

5 LAMU/ml Myceliophthora thermophila laccase and 25 µl trimethylamine were added to 10.0 ml of 40 mM Britton- Robinson buffer, pH 6.0, in a 50 ml volume glass bottle. The bottles were sealed with rubber cap. The reaction was started by adding 500 μl PPT mediator. Reaction time was 30 minutes at 37° C. The bottles were shaken manually during reactions. The malodour was scored by a panel of three persons.

| Enzyme | Mediator 500 μM | Malodour source | Score | |
|---|---|---|---|---|
| 0 | PPT | Trimethylamine | ++ | distinct fishy odour |
| 5 LAMU/ml | PPT | Trimethylamine | ± | almost no odour |

PPT and the laccase alone did not give any odour.

As can be seen of the table above almost all malodour caused from the trimethylamine disappeared after subjection to a mixture of laccase and PPT mediator.

Example 6

Reduction of Malodour (Short Fatty Acids)

5 LAMU/ml *Myceliophthora thermophila* laccase and 10 μl -10 butyric acid were added to 10.0 ml of 40 mM Britton-Robinson buffer, pH 6.0, in a 50 ml volume glass bottle. The bottles were sealed with rubber cap. The reaction was started by adding 500 μl PPT mediator. Reaction time was 30 minutes at 37° C. The bottles were shaken manually during reactions. The malodour was scored by a panel of three persons.

| Enzyme LAMU/ml | Mediator 500 μM | Malodour source | Score | |
|---|---|---|---|---|
| 0 | PPT | Butyric acid | ++ | distinct odour |
| 5 | PPT | Butyric acid | + | less odour than none-enzymatic treatment. |

PPT and the laccase alone did not give any odour.

Example 7

Reduction of Malodour (VSC) with Various Mediators

The ability to remove the malodour caused by methanethiol was tested using

1 μl of 1.5% methanethiol solution (0.11 mM) was added to a total volume of 2.0 ml of 20 mM Britton-Robinson buffer, pH 6.5, in a closed 20 ml glass bottle.

5 LAMU/ml *Myceliophthora thermofila* laccase and the mediator were added and reacted for 30 minutes at 37° C. under The reaction conditions: 37° C., 30 minutes, manual shaking during reactions

| Mediator (500 μM) | No enzyme Sniffing score | *Myceliophthora thermophila* laccase 5 LAMU/ml Sniffing score |
|---|---|---|
| none | ++ | ++ |
| caffeic acid | ++ | − |
| Chlorogenic acid | ++ | − |
| L-Tyrosine | ++ | + |
| p-hydroxybenzoic acid | ++ | + |
| Syringaldehyde | ++ | − |
| Methylsyringate | ++ | − |
| PPT | ++ | − |

−: no methanethiol odour
+: reduced methanethiol odour
++: strong methanethiol odour

Example 8

Reduction of Cooked Flavour from UHT-Milk

Two 10 ml samples of UHT-milk was treated as follow:

| | Chlorogenic acid (mM) | Laccase (LAMU/l) | Temp. (° C.) | Time (min) |
|---|---|---|---|---|
| Experimental sample | 0.1 | 10 | 40 | 30 |
| Control | 0.1 | none | 40 | 30 |

The UHT-milk used was skimmed milk treated at 140° C. (available from Klover Milk A.m.b.a., Frederikcia, Denmark).

The laccase used was derived from *Myceliophthora thermophila*, activity: 3760 LAMU/g (available from Novo Nordisk A/S, Denmark)

The sample was also added chlorogenic acid as mediator.

The oxygen concentration in UHT-milk was measured to 0.94 mg/l by using a Clark oxygen electrode (Rank Brothers, GB) and Oximeter Oxi 3000 (Wissenschaftlische Werkstätten G.m.b.H., DE). Propanal, butanal, hexanal, nonanal and di methyl sulphide was identified by GS-MS (Gas/Mass spectrometry) using a head space trapping (Büchi, Rotavapor R-134 with a purge and trap Concentrator auto sampler and sample pocket heater type Tekmar) coupled to Gas Chromatography-Mass spectometry equipment (Hewlett Packard G180OA GCD system). A pronounced cooked flavour was identified by a panel of 7 assessors.

The subsequent analysis of the samples showed that all of the above compounds had disappeared in the experimental sample while still being present in the control sample.

No cooked flavour could be identified by the sensory panel in the experimental sample while still found very pronounced in the control sample.

Example 9

Comparison Experiments Between *Myceliophthora thermophila* Laccase and Mushroom Tyrosinase A: 10 μl of 0.15 a sodium methanethiol solution (0.11 mM) was mixed with 500 μM mediator (final concentration) (0.5% Oolong tea extract when used) and 20 mM Britton-Robinson buffer (final concentration), pH 6.5 in 20 ml glass bottles to a total volume of 2.0 ml.

The bottles allowed to stand for 5 minutes at 37° C. Malodour was scored.

Enzymes were added and mediators used according to the table below.

| Mediator (500 µM or 5%) | Dosage mg enzyme protein/ml | rMtL | Tyrosinase |
|---|---|---|---|
| Chlorogenic acid | 0.005 | 9 | 3 |
|  | 0.01 | 0 | 2 |
| Methylsyringate | 0.1 | 0 | 4 |
| Oolong tea extract | 0.1 | 0 | 3 |

Ranking
4: Reference or odour as reference
3: Clear odour
2: Weak odour
1: Very weak odour
0: No odour B: Instead of sodium methanethiol 1 ml of the cultivated tongue plaque was used. Tongue plaque was collected from two subjects and inoculated in BHI (air was replaced with nitrogen). The inoculated plaque was cultivated overnight at 37° C.

The results are shown below.

| Mediator | Dosage mg enzyme protein/ml | rMtL | Tyrosinase |
|---|---|---|---|
| Chlorogenic acid | 0.1 | 2 | 3 |

As shown in the tablets, rMt laccase is more effective at removing malodour than Mushroom tyrosinase on enzyme protein weight basis.

Example 10

Reaction of rMt Laccase, the Mushroom Tyrosinase and the Mediators

500 µm mediator (except that the Oolong tea was 0.5%), 0.11 mM sodium methanethiol, 20 mM Britton-Robinson buffer, pH 6.5 was mixed in the same amounts and under the same conditions as in example 9.

ΔAbsorbance/min/mg enzyme protein was measured at 400 nm.

The result with different mediators is shown in the table below.

|  | ΔAbsorbance/min/mg enzyme protein | |
|---|---|---|
|  | rMt laccase | Tyrosinase |
| Chlorogenic acid | 21.8 | 1.49 |
| Syringaldehyde | 0.16 | 0.016 |
| Methylsyringate | 1.04 | 0.015 |
| Oolong tea extract | 1.35 | 0.03 |

As can be seen from the table rMt laccase develops colour more effectively than the mushroom tyrosinase, which indicates that rMt laccase produces a reactive o-quinone compound more effectively than the mushroom tyrosinase.

The results is obtained by dosing 0.01–0.2 mg/ml enzyme protein to 0.11 mM sodium methanethiol, 500 mM chlorogenic acid and 40 mm Britton-Robinson buffer, pH 6.5 at room temperature.

Example 11

Comparison Between rKt, rPp, rCc Laccase and Mushroom Tryosinase (Sigma)

The mixtures from example 8A was added enzymes according to the table below. Malodour was scored by a panel after 5 minute at 37° C.

| Donor | | Effect Ranking | | | |
|---|---|---|---|---|---|
| (500 µM or 0.5%) | Dosage mg enzyme protein/ml | rCcL | rPpL | rMtL | Tyrosinase |
| Chlorogenic acid | 0.01 | 0 | 0 | 0 | 3 |

Ranking
4: Reference or odor as reference
3: Clear odor
2: Weak odor
1: Very weak odor
0: No odor As shown in the table, the different laccases were more effective at removing malodour than Mushroom tyrosinase on enzyme protein weight basis.

Reaction of rMt laccase, the mushroom tyrosinase and the donors

500 µm mediator (except that the Oolong tea was 0.5%), 0.11 mM sdium methanethiol, 20 mM Britton-Robinson buffer, pH 6.5 was mixed in the same amounts and under the same conditions as in example 9.

ΔAbsorbance/min/mg enzyme protein was measured at 400 nm.

The result with different enzymes is shown in the table below.

|  | ΔAbsorbance/min/mg enzyme protein at 400 nm | | | |
|---|---|---|---|---|
|  | rCcL | rPpL | rMtL | Tyrosinase |
| Chlorogenic acid* | 7,01 | 21,6 | 26,2 | 1,04 |

As shown in the table, the laccases developed colour more effectively than the mushroom tyrosinase, which indicates that the laccases produces a reactive o-quinone compound more effectively than the mushroom tyrosinase.

Example 12

Comparison Between Peroxidase and Laccase

10 µl of 0.15% a sodium methanethiol solution (0.11 mM) was mixed with 500 µM chlorogenic acid and 20 mM Britton-Robinson buffer, pH 6.5 in 20 ml glass bottles to a total volume of 2.0 ml. In the case were peroxidases was used 1 mM hydrogenperoxid was added The bottles allowed to stand for 5 minutes at 37° C. Malodour was scored.

Enzymes were added according to the table below.

|  | mg enzyme protein/ml | | | |
| --- | --- | --- | --- | --- |
|  | $10^{-3}$ | $10^{-4}$ | $10^{-5}$ | $10^{-6}$ |
| rMtL | − | + | N.D. | N.D. |
| rCiP | − | − | + | + |
| Horse radish P-8125 | − | − | − | + |
| Horse radish P-8415 | − | − | − | + |
| Acid horse radish | − | − | − | + |

Odour ranking:
−: No odour
+: Odour
N.D.: Not done

As shown in the table, the peroxidases were as effective as laccase at removing malodour but at a lower concentration.
Reaction of rMt laccase and peroxidases with chlorogenic acid The Δabsorbance of solutions containing 500 μM chlorogenic acid, 1 mM hydrogen peroxide (only for the peroxidases), 0.11 mM sodium methanethiol, 20 mM Britton-Robinson buffer pH 6.5 at room temperature and different enzymes was measured at 400 nm.
Peroxidase:

| | ΔAbsorbance/min/mg enzyme protein at 400 nm | | | |
| --- | --- | --- | --- | --- |
| | rCiP | Horse radish P-8125 | Horse radish P-8415 | Acid horse radish |
| Chlorogenic acid | 9480 | 11800 | 14200 | 18600 |

Laccase and Tyrosinase:

| | ΔAbsorbance/min/mg enzyme protein at 400 nm | | | |
| --- | --- | --- | --- | --- |
| | rCcL | rPpL | rMtL | Tyrosinase |
| Chlorogenic acid* | 7,01 | 21,6 | 26,2 | 1,04 |

As shown in the tables, the peroxidases developed colour more effectively than the laccases and the mushroom tyrosinase, which indicates that the peroxidases produces the reactive o-quinone compound more efficiently. The table also shows that laccase developes colour more effectively than tyrosinase.

We claim:

1. A composition comprising
   (i) a laccase obtained from a strain selected from the group consisting of Coprinus, Polyporus and Myceliophthora, and
   (ii) a mediator selected from the group consisting of chlorogenic acid, Oolong tea extract, and caffeic acid and esters thereof.

2. The composition of claim 1, wherein the laccase is obtained from a strain of Myceliophthora.

3. A composition comprising
   (i) a peroxidase obtained from a strain of Coprinus, and
   (ii) a mediator selected from the group consisting of chlorogenic acid, Oolong tea extract, and caffeic acid and esters thereof.

4. The composition of claim 1, further comprising a surfactant.

5. An oral care product comprising
   (i) a laccase obtained from a strain selected from the group consisting of Coprinus, Polyporus, and Myceliophthora, and
   (ii) a mediator selected from the group consisting of chlorogenic acid, Oolong tea extract, and caffeic acid and esters thereof.

6. The oral care product of claim 5, wherein the laccase is obtained from a strain of Myceliophthora.

7. An oral care product comprising
   (i) a peroxidase obtained from a strain of Coprinus, and
   (ii) a mediator selected from the group consisting of chlorogenic acid, Oolong tea extract, and caffeic acid and esters thereof.

8. The oral care product of claim 7, wherein the product is toothpaste, dental cream, gel or tooth powder, odontic, mouth washes, pre- or post-brushing rinse formulations, chewing gum, lozenges, or candy.

9. A food product comprising
   (i) a laccase obtained from a strain selected from the group consisting of Coprinus, Polyporus, and Myceliophthora, and
   (ii) a mediator selected from the group consisting of chlorogenic acid, Oolong tea extract, and caffeic acid and esters thereof.

10. The food product of claim 9, wherein the laccase is obtained from a strain of Myceliophthora.

11. A food product comprising
    (i) a peroxidase obtained from a strain of Coprinus, and
    (ii) a mediator selected from the group consisting of chlorogenic acid, Oolong tea extract, and caffeic acid and esters thereof.

12. A hygiene product comprising
    (i) a laccase obtained from a strain selected from the group consisting of Coprinus, Polyporus, and Myceliophthora, and
    (ii) a mediator selected from the group consisting of chlorogenic acid, Oolong tea extract, and caffeic acid and esters thereof.

13. The hygiene product of claim 12, wherein the laccase is obtained from a strain of Myceliophthora.

14. A hygiene product comprising
    (i) a peroxidase obtained from a strain of Coprinus, and
    (ii) a mediator selected from the group consisting of chlorogenic acid, Oolong tea extract, and caffeic acid and esters thereof.

15. The hygiene product of claim 12, wherein the product is diapers, adult incontinence products, training pants, feminine napkins, or tampons.

16. A toiletry product comprising
    (i) a laccase selected from a strain selected from the group consisting of Coprinus, Polyporus, and Myceliophthora, and
    (ii) a mediator selected from the group consisting of chlorogenic acid, Oolong tea extract, and caffeic acid and esters thereof.

17. The toiletry product of claim 16, wherein the laccase is obtained from a strain of Myceliophthora.

18. A toiletry product comprising
    (i) a peroxidase obtained from a strain of Coprinus, and
    (ii) a mediator selected from the group consisting of chlorogenic acid, Oolong tea extract, and caffeic acid and esters thereof.

19. The toiletry product of claim 16, wherein the product is a soap bar.

* * * * *